United States Patent
Inagi et al.

(10) Patent No.: US 6,582,720 B1
(45) Date of Patent: Jun. 24, 2003

(54) MEDICINAL COMPOSITIONS ADHERING TO STOMACH/DUODENUM

(75) Inventors: Toshio Inagi, Mishima (JP); Hiroyuki Shirai, Fuji (JP); Norikazu Yamaguchi, Fuji (JP); Takeshi Nishino, Kyoto (JP)

(73) Assignee: Kowa Co., Ltd., Nagoya (JP)

(*) Notice: Subject to any disclaimer, the term of this patent is extended or adjusted under 35 U.S.C. 154(b) by 0 days.

(21) Appl. No.: 09/600,885

(22) PCT Filed: Mar. 17, 1999

(86) PCT No.: PCT/JP99/01311
§ 371 (c)(1),
(2), (4) Date: Sep. 7, 2000

(87) PCT Pub. No.: WO99/48532
PCT Pub. Date: Sep. 30, 1999

(30) Foreign Application Priority Data

Mar. 20, 1998 (JP) .......................... 10-072098
Mar. 20, 1998 (JP) .......................... 10-072099

(51) Int. Cl.$^7$ ............................................. A61F 13/00
(52) U.S. Cl. ................ 424/434; 424/441; 424/407; 424/427; 424/428; 514/558
(58) Field of Search ............... 514/558; 424/441, 424/407, 427, 428, 434

(56) References Cited

U.S. PATENT DOCUMENTS 4,765,990 A * 8/1988 Sugimoto et al. ........... 424/494
5,576,025 A 11/1996 Akiyama et al.
5,731,006 A 3/1998 Akiyama et al.
5,948,773 A 9/1999 Akiyama et al.
5,955,502 A * 9/1999 Hansen et al. ............. 514/558
6,090,412 A * 7/2000 Hashimoto et al. ........ 424/490

FOREIGN PATENT DOCUMENTS

| JP | 9-104640 | 4/1997 |
| JP | 10-167985 | 6/1998 |
| WO | WO 98/42311 | 1/1998 |

* cited by examiner

Primary Examiner—Jose G. Dees
Assistant Examiner—Robert DeWitty
(74) Attorney, Agent, or Firm—Oblon, Spivak, McClelland, Maier & Neustadt, P.C.

(57) ABSTRACT

The present invention provides a gastric and/or duodenal adhesive pharmaceutical composition obtained by coating a composition, which comprises a medicament acting at the stomach and/or duodenum and one or more of ingredients selected from water insoluble polymers, polyglycerin fatty acid esters, lipids and waxes, with a polymer having adhesive capacity onto the surface of the mucosa of a digestive tract under acid conditions and separates from the mucosa of the digestive tract in neutral or alkaline conditions. This composition adheres only to the mucosa of the stomach and/or duodenum and releases the medicament over long hours so that sufficient effects are available by a small amount of the medicament.

14 Claims, 3 Drawing Sheets

The covering ratio of the preparation at a particle size of 100 μm was designated as 100.

Relation between particle size and adhesion

The covering ratio of the preparation at a particle size of 100 μm was designated as 100.

Relation between particle size and adhesion

Transition of medicament

Eradication effects of preparation

Administration of 0.1 mg/kg in terms of AMOX

Influence of release time on eradication effects

MEDICINAL COMPOSITIONS ADHERING TO STOMACH/DUODENUM

TECHNICAL FIELD

The present invention relates to a pharmaceutical composition which adheres only to a gastric mucosa and duodenal mucosa and is controlled in the release of its medicament.

BACKGROUND ART

When effective use of a medicament is considered, a preparation controlled in the release of the medicament thereof, particularly, a sustained release preparation has great advantages such as decrease in the frequency of administration, maintenance of the blood level for a predetermined time and the like, because it can continuously release the medicament over long hours. Sustained release preparations have therefore been investigated from various aspects.

Since the medicament of a sustained release preparations is mainly absorbed at the intestine, many of the preparations are designed to gradually release the medicament while they pass through the whole digestive tract. On the contrary, preparations designed to exhibit their efficacy not after adsorbed by the intestine but topically at the stomach or duodenum are not so many.

As a preparation intended to cause the medicament to act in the stomach, reported have been a preparation having intragastric retention heightened by imparting it with a floating property (Daviss S S et al. Pharm. Res. 208–213 (1986)), a preparation whose contact ratio to the surface of a mucosa has been improved by increasing the specific gravity of it (Devereux J E et al. Pharmacol, 42, 500–501 (1990)) and the like. These preparations however are not sufficient in retention.

In addition, a preparation which adheres onto the mucosa of a digestive tract by gelation of a polymer, which has been incorporated in the preparation, with water has been proposed (Japanese Patent Application Laid-Open No. Hei 5-132416). This preparation however lacks in adhesion selectivity to an intended digestive tract so that it is impossible to adhere this preparation only to the gastric and duodenal mucosae.

An object of the present invention is therefore to provide a preparation which adheres only to the gastric and duodenal mucosa, is controlled in the release of its medicament and has excellent pharmacological effects selectively for the stomach and duodenum.

DISCLOSURE OF THE INVENTION

With the foregoing in view, the present inventors have carried out an extensive investigation. As a result, it has been found that by controlling the release of a medicament by an ingredient selected from water insoluble polymers, polyglycerin fatty acid esters, lipids and waxes, and imparting the medicament with selective adhering capacity only to the gastric and duodenal mucosae by using a polymer which adheres to the surface of the mucosa of a digestive tract under acid conditions but does not adhere under neutral or alkali conditions, the medicament acts on the gastric and duodenal mucosa over long hours but quickly excreted from the intestine, which makes it possible to provide a preparation exhibiting high pharmacological action at a low concentration of the medicament, leading to the completion of the present invention.

The present invention therefore provides a gastric and/or duodenal adhesive pharmaceutical composition obtained by coating a composition, which contains a medicament exhibiting action in the stomach and/or duodenum and an ingredient selected from water insoluble polymers, polyglycerin fatty acid esters, lipids and waxes, with a polymer which has adhering capacity to the surface of the mucosa of a digestive tract under acid conditions but separates from the mucosa of the digestive tract under neutral or alkaline conditions.

BEST MODES FOR CARRYING OUT THE INVENTION

Figure 1:
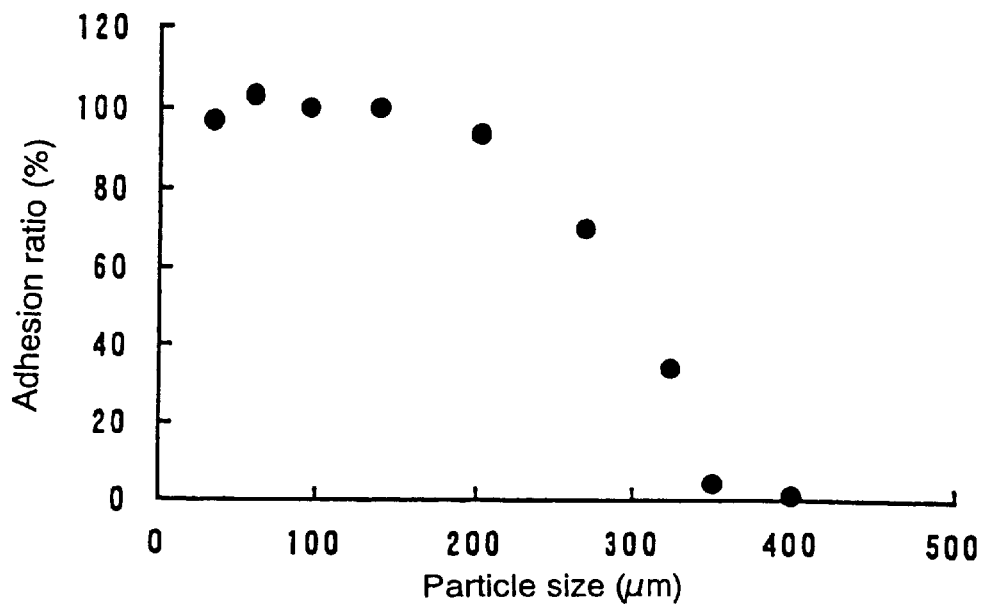
FIG. 1 illustrates the relation between the particle size of a preparation and its adhesion ratio to cells.

Although no particular limitation is imposed on the polymer which has adhering capacity to the surface of a gastric and/or duodenal mucosa under acid conditions and separates from the mucosa of a digestive tract under neutral or alkaline conditions (said polymer will hereinafter be called "pH-dependent adhesive polymer"), polymers which are soluble in a solution of at least pH 4 and have an anionic group are preferred. Examples of such a pH-dependent adhesive polymer include:

(1) Natural polymers: purified shellac and white shellac; and (2) Synthetic polymers:

Cellulose derivative polymers: hydroxypropylmethylcellulose phthalate, hydroxypropylmethylcellulose acetate succinate, carboxymethylethyl cellulose, cellulose acetate trimellitate, cellulose acetate phthalate, etc., Acrylic polymers: polymers obtained from acrylic acid and/or methacrylic acid, polymers obtained from acrylic acid and/or methacrylic acid and a carboxylic ester, etc. and Polyvinyl alcohol type polymers: polyvinyl acetate phthalate, etc.

As the pH dependent adhesive polymers used in the present invention, those having a carboxyl group are particularly preferred, with those obtained from acrylic acid and/or methacrylic acid being more preferred and those obtained from acrylic acid and/or methacrylic acid and a carboxylic ester being still more preferred. Examples of the carboxylic ester used herein include acrylic esters and methacrylic esters such as methyl acrylate, ethyl acrylate, n-propyl acrylate, isopropyl acrylate, n-butyl acrylate, isobutyl acrylate, t-butyl acrylate, 2-hydroxyethyl acrylate, 2-hydroxypropyl acrylate, methyl methacrylate, ethyl methacrylate, n-propyl methacrylate, isopropyl methacrylate, 2-hydroxyethyl methacrylate, 2-hydroxypropyl methacrylate, n-butyl methacrylate, isobutyl methacrylate and t-butyl methacrylate.

Among them, a methacrylic acid-methyl methacrylate copolymer is preferred, with that having a methacrylic acid content of 20 to 60%, for example, Eudragit L100 or S100 being particularly preferred.

These pH dependent adhesive polymers may be used either singly or in combination.

In the present invention, the ingredient selected from water insoluble polymers, polyglycerin fatty acid esters, lipids and waxes (which may hereinafter be called "water-insoluble ingredient") is an ingredient for controlling the release of active ingredients.

No particular limitation is imposed on the water insoluble polymers used in the present invention insofar as they are sustained release bases ordinarily employed for preparations. These polymers may be used either singly or in combination. As such polymers, following ones may be mentioned by way of example.

Cellulose type polymers: crystalline cellulose, ethyl cellulose, hydroxymethylcellulose phthalate, hydroxymethylcellulose acetate succinate, carboxymethylethyl cellulose, cellulose acetate phthalate, [etc.] Among them, ethyl cellulose is particularly preferred.

No particular limitation is imposed on the polyglycerin fatty acid esters used in the present invention and fatty acid esters of polyglycerin such as di-, tri- or higher-glycerin may be used. As the fatty acid portion of the polyglycerin fatty acid esters, $C_{8-30}$ fatty acids are preferred, while as the polyglycerin portion, diglycerin to eicosaglycerin are preferred.

Specific examples of the polyglycerin fatty acid ester include diglyceryl monostearate, tetraglyceryl monostearate, hexaglyceryl monostearate, decaglyceryl monostearate, tetraglyceryl tristearate, decaglyceryl tristearate, tetraglyceryl pentastearate, hexaglyceryl pentastearate, hexaglyceryl monooleate, decaglyceryl monooleate, triglyceryl dioleate, tetraglyceryl dioleate, tetraglyceryl pentaoleate, hexaglyceryl pentaoleate, triglyceryl dilinoleate, tetraglyceryl dilinoleate, hexaglyceryl dilinoleate, tetraglyceryl monopalmitate, hexaglyceryl monopalmitate, decaglyceryl monopalmitate, tetraglyceryl tripalmitate and hexaglyceryl tripalmitate.

Examples of the lipid used in the present invention include higher fatty acids and salts thereof, higher alcohols and fatty acid glycerin esters and those of the wax include waxes and hydrocarbons. Examples of the higher saturated fatty acid or salt thereof include $C_{8-30}$ fatty acids and salts thereof such as stearic acid, magnesium stearate and aluminum stearate. Examples of the higher alcohol include $C_{10-24}$ aliphatic alcohols such as stearyl alcohol and cetyl alcohol. As the fatty acid glycerin ester, not only triglycerides with a fatty acid but also monoglycerides and diglycerides therewith may be used. Examples of the waxes include carnauba wax and bees wax, while those of the hydrocarbon include microcrystalline wax and paraffin.

The above-described water-insoluble ingredients, that is, water-insoluble polymers, polyglycerin fatty acid esters, lipids and waxes, may be used either singly or in combination.

With a view to freely controlling the releasability of the medicament from a preparation, a water soluble polymer may be added in any ratio to the above-described water-insoluble ingredient. Examples of such a polymer include polyethylene glycol, hydroxyethyl cellulose, hydroxypropyl cellulose, aminoalkyl methacrylate copolymers and polyvinylacetal diethylaminoacetate.

In order to freely control the releasability in the present invention, the water soluble polymer is preferably added in an amount ranging from 0.1 to 60 wt. % to the above-described water-insoluble ingredient.

As the medicament used in the present invention, medicaments which act in the stomach or duodenum are suited. Examples of such medicaments include antiacids, gastric mucosa protectors, $H_2$ blockers, proton pump inhibitors (PPIs), antibiotics and urease inhibitors.

Examples of the antiacid used in the present invention include magnesium hydroxide and aluminum magnesium silicate.

Examples of the gastric mucosa protector used in the present invention include methyl methionine sulfonyl chloride (MMSC), ecabet sodium, sucralfate and cetraxate hydrochloride.

Examples of the $H_2$ blocker used in the present invention include famotidine, cimetidine, roxatidine acetate and ranitidine.

Examples of the PPIs used in the present invention include omeprazole and lansoprazole.

Examples of the urease inhibitor used in the present invention include acetohydroxamic acid and caprylohydroxamic acid.

Examples of the antibiotic used in the present invention include anti-*Helicobacter pylori* active substances, bismuth salts and quinolone type compounds, of which anti-*Helicobacter pylori* active substances are preferred. Examples of the anti-*Helicobacter pylori* active substance include penicillin type antibiotics (such as amoxicillin and ampicillin), macrolides (such as erythromycin and clarithromycin) and tetracycline type antibiotics (such as tetracycline, minocycline and streptomycin). Among these antibiotics, penicillin type antibiotics are preferred, with amoxicillin (which will hereinafter be abbreviated as "AMOX") having high antibacterial property against *Helicobacter pylori* being particularly preferred.

In the composition of the present invention, the content of the medicament may be determined as needed depending on the nature of the medicament or preparation. Usually, a content of 0.01 to 95 wt. % or so is preferred, with a range of from 0.1 to 90 wt. % being particularly preferred. The using amount of the water-insoluble ingredient may be determined depending on the nature of the ingredient, release time of the medicament or the like. It is however preferred to incorporate it in an amount of 0.1 to 95 wt. % in the composition, with 1 to 60 wt. % being particularly preferred. The pH-dependent adhesive polymer is preferably incorporated in an amount of 0.1 to 95 wt. % in the composition, with 1 to 50 wt. % being particularly preferred.

To the composition of the present invention, ordinarily employed additives used for the preparation of a solid pharmaceutical may be added. Examples include following ones:

(1) Excipient: lactose, corn starch, talc, powdered sugar, light anhydrous silicic acid, calcium carbonate, magnesium carbonate, etc.
(2) Binder: starch, sucrose, gelatin, powdered acacia, carboxymethyl cellulose, carboxymethylcellulose sodium, hydroxypropyl cellulose, hydroxypropylmethyl cellulose, polyvinyl pyrrolidone, pullulan, dextrin, etc.
(3) Plasticizer: polyethylene glycol, triethyl citrate, etc.

In addition, colorants, corrigents, adsorbents, antiseptics, humectants and antistatic agents can be used as additives. The amount of such an additive may be determined as needed within an extent neither impairing pH-dependent adhesion to the gastric mucosa nor having adverse effects on the releasability of the medicament.

The composition of the present invention comprises a medicament, an additive if necessary, and the above-described insoluble ingredient and it has been coated with a pH-dependent adhesive polymer. Here, the composition comprising a medicament, a necessary additive and the above-described water-insoluble ingredient may be a composition having a medicament or medicament-additive mixture coated with the above-described water-insoluble ingredient or a matrix containing the medicament, necessary additive and the above-described water-insoluble ingredient as a mixture. The former one is however preferred. The term "coating" as used herein means not only the uniform coating of the whole surface of a particle but also partial coating of the surface of the particle.

Although the release time of the medicament from the preparation may be determined freely in consideration of the properties of the medicament to be selected or the like, continuous and longer release time is desired in order to fully exhibit the properties of the preparation, that is, to adhere to the gastric mucosa and allow the medicament to directly act thereon. In addition, the release of the medicament is desirably completed while the preparation has still adhered to and retained in the gastric mucosa. Influences of gastric juice, metabolism of the gastric epitheliocytes, meal and the like must of course be taken into consideration. The release time of the medicament from the preparation is desired to be 2 to 8 hours, judging from the above-described factors. The release time may be controlled by a ratio of the water-insoluble ingredient to a water soluble polymer, amount of the water-insoluble ingredient or the like.

The particle size of the pharmaceutical composition of the present invention is preferred to fall within a range of 30 to 300 μm from the viewpoint of adhesion to the gastric and/or duodenal mucosa, with a range of 75 to 300 μm, moreover 100 to 250 μm being particularly preferred.

In the case where the pharmaceutical composition of the present invention is a preparation coated with the above-described water-insoluble ingredient, it is prepared, for example, by forming medicament-containing particles by a conventionally employed granulator or the like and then coating the particles with the above-described water-insoluble ingredient and pH dependent adhesive polymer successively. For granulation, fluidized bed granulation, high shear granulation, extrusion granulation or the like can be adopted. For coating, conventionally employed method such as pan coating or fluidized bed coating can be adopted. For the coating agent in the form of a solution or dispersion containing water or an organic solvent, spray coating can also be adopted.

In the case where the composition containing a medicament and the above-described water-insoluble ingredient is in the form of a matrix, it can be prepared by dissolving the above-described water-insoluble ingredient in a suitable organic solvent, kneading the resulting solution with the medicament, and then drying and pulverizing the kneaded mass, or dissolving the above-described water-insoluble ingredient containing the medicament in a suitable solvent, dispersing the resulting solution in a solution immiscible with the solvent and then evaporating the solvent by heating to form particles; and then coating the particles with a pH-dependent adhesive polymer.

There is no particular limitation imposed on the nature of the organic solvent. Examples include alcohols such as methanol, ethanol and isopropanol, ketones such as acetone and halogenated hydrocarbons such as chloroform and dichloromethane. In the coating agent or matrix, the above-described additive or the like may be incorporated.

EXAMPLES

The present invention will hereinafter be described more specifically by examples and tests. It should however be borne in mind that the present invention is not limited by these examples.

Example 1

In accordance with the formulation shown in Table 1, a gastric and/or duodenal mucosa adhesive preparation was prepared using a fluidized-bed coating machine. Namely, to 3000 g of anhydrous calcium hydrogenphosphate (average particle size: 150 μm), a solution of 75 g of riboflavin phosphate in 3 liters of water was sprayed and dried, followed by spraying and coating of a solution of 400 g of ethyl cellulose in 4 liters of ethanol. After drying, a solution of 500 g of a methacrylic acid-methyl methacrylate copolymer ("Eudragit L100", trade name) and 50 g of triethyl citrate in 5 liters of ethanol was sprayed for coating, whereby a yellow gastric and/or duodenal mucosa adhesive preparation 1 was prepared.

Comparative Example 1

In a similar manner to Example 1, a solution of 75 g of riboflavin phosphate in 3 liters of water was sprayed to 3000 g of anhydrous calcium hydrogenphosphate (average particle size: 150 μm) and dried, followed by coating only with a solution of 400 g of ethyl cellulose in 4 liters of ethanol, whereby Comparative preparation 1 was obtained.

TABLE 1

|  | Adhesive preparation 1 | Comparative preparation 1 |
|---|---|---|
| Anhydrous calcium hydrogenphosphate ("Fujikarin SG", trade name) | 3000 g | 3000 g |
| Riboflavin phosphate | 75 g | 75 g |
| Ethyl cellulose | 400 g | 400 g |
| Methacrylic acid-methyl methacrylate copolymer ("Eudragit L100", trade name) | 500 g | — |
| Triethyl citrate | 50 g | — |

Referential Example 1

In accordance with the formulation shown in Table 2, gastric and/or duodenal mucosa adhesive compositions were prepared. Namely, 20 g of a methacrylic acid-methacrylate copolymer ("Eudragit L100", trade name) and 2 g of triethyl citrate were dissolved in 50 ml of ethanol, followed by the addition of 25 g of a medicament and 75 g of an excipient. The resulting mixture was thoroughly mixed under heating to 60° C. and then dried. The dried mixture was pulverized, followed by classification, whereby preparations having average particle sizes of about 30, 70, 100, 150, 200, 270, 325, 350 and 400 μm, respectively were obtained.

TABLE 2

| Barium sulfate | 25 g |
|---|---|
| Corn starch | 75 g |
| Methacrylic acid-methyl methacrylate copolymer ("Eudragit L100", trade name) | 20 g |
| Triethyl citrate | 2 g |
| (Ethanol) | 50 ml |

Example 2

In a fluidized-bed granulator, 250 g of AMOX and 250 g of an excipient, out of the ingredients shown in Table 3, were charged, followed by spraying thereto a solution of 40 g of ethyl cellulose in 400 ml of ethanol and granulation. Then, the resulting granules were coated with a solution of 150 g of ethyl cellulose in 1.5 liters of ethanol and then with a solution of 125 g of a methacrylic acid-methyl methacrylate copolymer ("Eudragit L100", trade name) and 25 g of triethyl citrate in 1.5 liters of ethanol, whereby a preparation was formed. The resulting preparation was classified, whereby spherical fine particles passing through not 150 mesh but 80 mesh (which will hereinafter be abbreviated as "80/150 mesh") were obtained as Preparation (1). In the next place, 41.9 g of AMOX and 458.1 g of an excipient were charged in a fluidized-bed granulator, followed by granulation. The resulting granules were coated in a similar manner to that described for Preparation (1), whereby Preparation (2) was obtained. In the third place, 41.9 g of AMOX and 458.1 g of an excipient were charged in a fluidized-bed granulator and granulated in a similar manner to that described for Preparation (2), followed by coating with a solution of 112 g of ethyl cellulose and 38 g of polyethylene glycol 6000 in 1.5 liters of ethanol for the control the releasability. The methacrylic acid-methyl methacrylate copolymer ("Eudragit L100", trade name) was coated in a similar manner to that described for Preparation (1) or (2), whereby Preparation (3) was obtained. In the fourth place, 250 g of AMOX and 250 g of an excipient were charged in a fluidized-bed granulator, followed by granulation in a similar manner to (1). The resulting granules were coated with ethyl cellulose and then with a solution of methacrylic acid-methyl methacrylate copolymers ("Eudragit L100", trade name: 93.7 g, "Eudragit S100", trade name: 31.3 g) and 25 g of triethyl citrate in 1.5 liters of ethanol, whereby Preparation (4) was obtained.

TABLE 3

|  | (1) | (2) | (3) | (4) |
|---|---|---|---|---|
| AMOX | 250 g | 41.9 g | 41.9 g | 250 g |
| Corn starch | 250 g | 250 g | 250 g | 250 g |
| Mannitol | — | 208.1 g | 208.1 g | — |
| Ethylcellulose | 190 g | 190 g | 152 g | 190 g |
| PEG6000 | — | — | 38 g | — |
| Methacrylic acid-methyl methacrylate copolymers: | | | | |
| ("Eudragit L100", trade name) | 125 g | 125 g | 125 g | 93.7 g |
| ("Eudragit S100", trade name) | — | — | — | 31.3 g |
| Triethyl citrate | 25 g | 25 g | 25 g | 25 g |
| Release time (hour) | 6 | 6 | 2 | 6 |

Comparative Example 2

By using a polymer forming a gel with water, said polymer being described in Japanese Patent Application Laid-Open No. Hei 5-132416, a preparation adhesive onto the mucosa of a digestive tract was prepared. Described specifically, 85 g of stearic acid was dissolved at 70° C., followed by the addition of 15 g of an acrylic acid type polymer ("Hibiswako 104", trade name). After thorough mixing for 10 minutes, the resulting mixture was cooled and solidified. The resulting solid was subjected to pulverization and classification, whereby a preparation having a particle size of about 150 µm was prepared.

Test 1

Investigation of intragastric retention brought by a pH dependent adhesive polymer Preparations obtained in Example 1 and Comparative Example 1 were each suspended in an amount of 10% (W/V) in the JP first liquid. To rats (SD rats, 8 weeks old) fasted for 24 hours, 2 ml of the resulting suspension was administered. Each of one hour and three hours after the administration, the stomach was enucleated and retention of the preparation in the stomach was investigated. As a result, the retention of the yellow preparation of Example 1 in the stomach each of one hour and three hours after the administration was confirmed, while the retention of the yellow preparation of Comparative Example 1 was not confirmed after one hour. From the results, it has been confirmed that the addition of a methacrylic acid-methyl methacrylate copolymer is necessary for the retention of the preparation in the gastric mucosa.

Test 2

Investigation on the adhesion depending on a particle size

Preparations obtained in Referential Example 1, which differed in the particle size, were each suspended in an amount of 10% (W/V) in the JP first liquid. Two ml of the resulting suspension was administered to human fibroblasts which had been cultured on a plastic slip until the confluent condition. By being left over standstill for one minute, the preparation was adhered to the cells. After adhesion, the plastic slip was washed in the JP first liquid. Then, the weight of the preparation remained on the plastic slip was measured and the amount of the preparation adhered was calculated. In addition, from the amount adhered, the covered area of the preparation was calculated in accordance with the following formula as an indication of adhesion of the preparation to cells.

<Calculation formula> particle size : r, specific gravity of the preparation: d, amount adhered: W

Weight per particle: $w = 4/3 \times \pi \times (r/2)^3 \times d$

Number of particles adhered: $N = W/w$

Area covered by one particle: $s = \pi \times (r/2)^2$

Total covered area: $S = N \times s$

The results are shown in FIG. 1. From the results, concerning the adhesion of the preparation to cells, no change was recognized in the adhesion of the particles having a particle size up to 200 µm, gradual deterioration in adhesion was recognized in the particles having a particle size greater than 200 µm and adhesion was not recognized in the particles having a particle size of 350 µm or greater. From the above finding, it has been confirmed that pH-dependent adhesion of the preparation occurs within a particle size up to 300 µm or so and constantly high adhesion is available when the particle size is up to 200 µm or so.

Test 3

Figure 2:
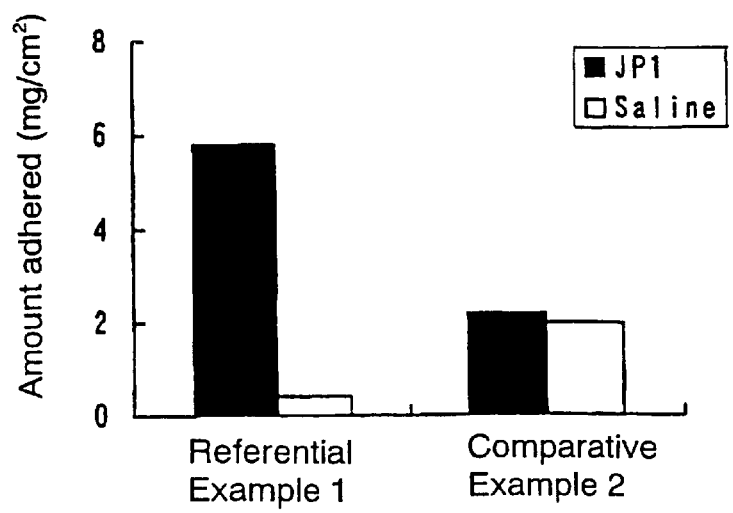
FIG. 2 illustrates the relation between pH and adhesion.

The adhesion to the human fibroblasts in each of solutions different in pH was studied using the preparation of Referential Example 1 containing a methacrylic acid-methyl methacrylate copolymer and having a particle size of 150 µm and the comparative preparation containing an acrylic acid type polymer and prepared in Comparative Example 2. The results are shown in FIG. 2.

From the results, the preparation containing a methacrylic acid-methyl methacrylate copolymer exhibited good adhesion in JP1 (pH 1.2) but no adhesion was observed in a physiological saline adjusted to pH 6. The comparative preparation containing an acrylic acid type polymer, on the other hand, exhibited no difference in adhesion depending on pH. From the above finding, it has been recognized that the adhesion brought by a methacrylic acidmethyl methacrylate copolymer depends on pH and has high topical selectivity.

Test 4

Transition of medicament by mucoadhesion

Figure 3:
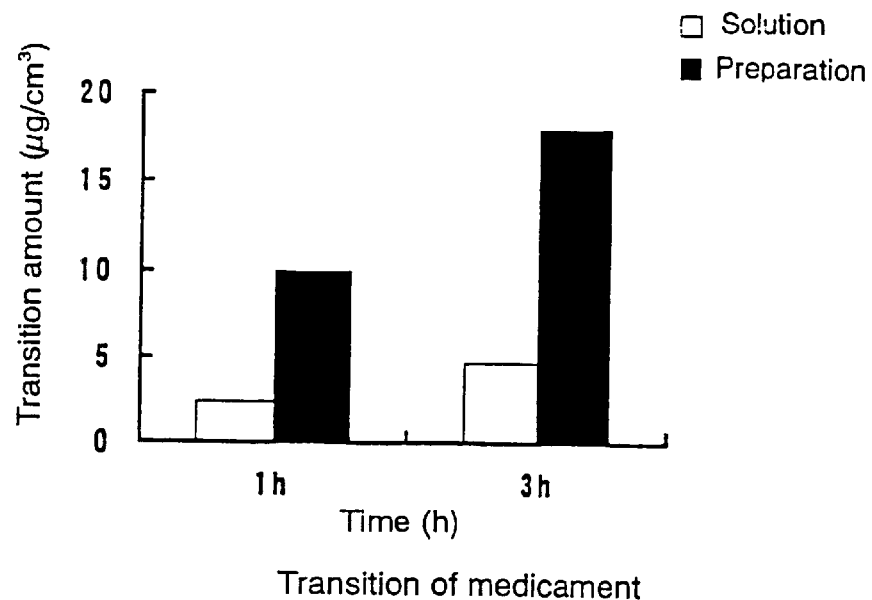
FIG. 3 illustrates transition of a medicament to gelatin.

A solidified 20% gelatin was placed in a solution as a gastric mucosa model. To the gelatin, 50 mg (1 mg in terms of riboflavin phosphate) of the gastric and/or duodenal mucosa adhesive preparation prepared in Example 1 and 1 mg of riboflavin phosphate were each administered, followed by stirring at 25 rpm to remove a concentration gradient. After 1 hour and 3 hours, amounts of the medicament transferred to the gelatin were measured, respectively. The results are shown in FIG. 3.

From the results, higher transition was confirmed in the gelatin administered with the gastric and/or duodenal mucosa adhesive preparation compared with that administered with the solution, indicating that more effective pharmacological action can be attained and dosage can be reduced by adhering the preparation directly to the stomach and/or duodenum and releasing the medicament from the preparation.

Test 5

Effects of AMOX-containing gastric and/or duodenal mucosa adhesive preparation

Figure 4:
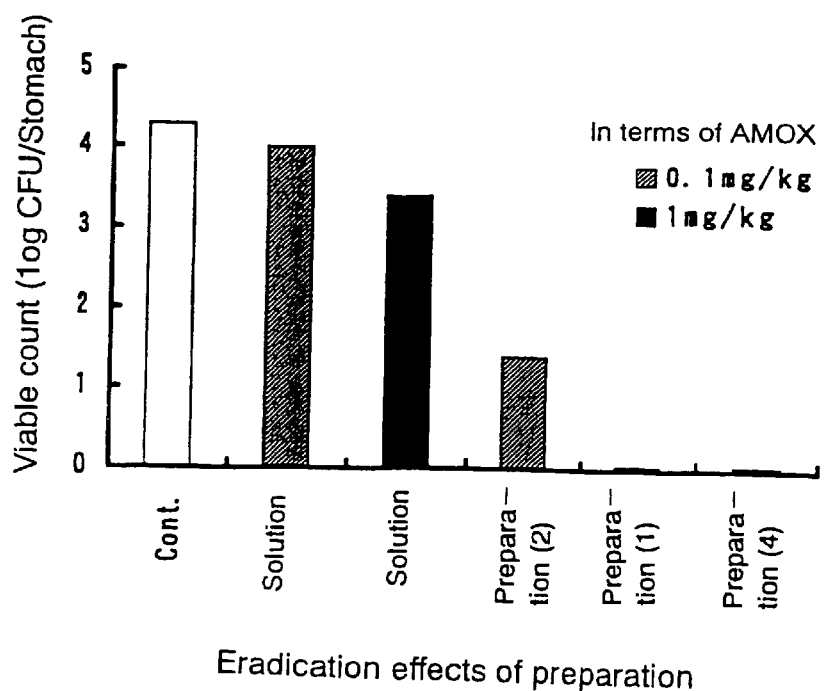
FIG. 4 illustrates eradication effects.

Each of the AMOX-containing gastric and/or duodenal mucosa adhesive compositions [(1), (2) and (4) in Table 3] prepared in Example 2 was suspended in a 0.1% tragacanth solution for use as a preparation-administering solution. In a similar tragacanth solution, AMOX powder was suspended for use as an administering solution. A ddY mouse fasted for 24 hours was orally and endogastrically infected with *Helicobacter pylori* ATCC 43504 (which will hereinafter be abbreviated as "HP"; $10^9$ viable count x 3/mouse). After 27 days, the respective solutions of preparations and solution were adjusted to contain AMOX in amounts of 0.1 mg/kg (preparation (2)) and 1 mg/kg (preparations (1) and (4)) and then orally administered for 5 straight days. From the mouse, its stomach was excised 24 hours after the final administration and a solution of the disrupted stomach was inoculated on an HP selective medium. After incubation for 8 days under microaerophilic conditions, the viable count was measured. The viable count of HP is shown in FIG. 4. From the results, it has been confirmed that compared with the group administered with the solution-administering group, the group administered with the AMOX containing gastric and/or duodenal adhesive preparation exhibited higher eradication effects.

Test 6

Figure 5:
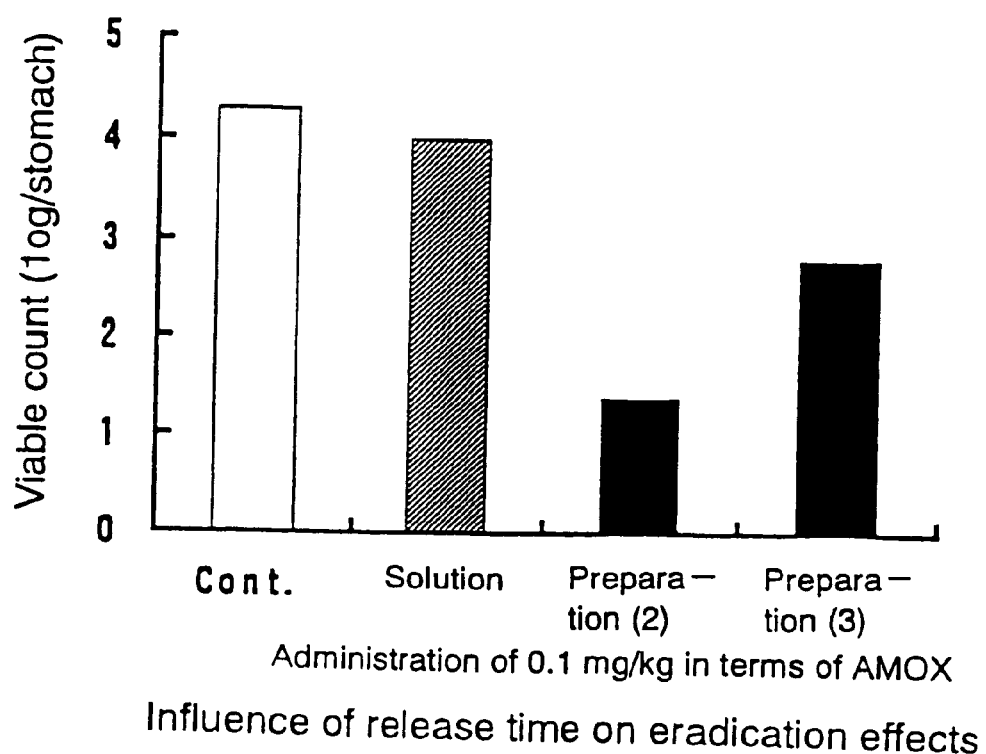
FIG. 5 illustrates the eradication effects of preparations different in release time.

Eradication effects of AMOX-containing gastric and/or duodenal mucosa adhesive preparation depending on release time The AMOX-containing gastric and/or duodenal mucosa adhesive preparations [(2) and (3) in Table 3] prepared in Example 2 were each suspended in a 0.1% tragacanth solution. The resulting suspension was adjusted to contain AMOX in an amount of 0.1 mg/kg, followed by administration for 5 straight days to a ddY mouse infected with HP in a similar manner to Test 4. The viable count was measured as in Test 5 and results are shown in FIG. 5. From the results, two AMOX-containing gastric and/or duodenal mucosa adhesive preparations were recognized to have higher eradication effects than the solution. Moreover, the preparation (2) with a longer release time of AMOX (6 hours) was recognized to have higher eradication effects than the preparation (3) with a shorter AMOX release time (2 hours). From the above finding, it has been recognized that effective eradication can be carried out by controlled release of a medicament.

Example 3

In 20 ml of ethanol, 6 g of a methacrylic acid-methyl methacrylate copolymer ("Eudragit L100", trade name) and 1.2 g of triethyl citrate were charged and dissolved thoroughly. To the resulting solution, 8 g of tetraglyceryl monostearate was added. After drying, the resulting mixture was subjected to granulation and classification, whereby a preparation having an average particle size of 150 μm was obtained.

Example 4

In 20 ml of ethanol, 6 g of a methacrylic acid-methyl methacrylate copolymer ("Eudragit L100", trade name) and 1.2 g of triethyl citrate were charged and dissolved thoroughly. The resulting solution was mixed with 8 g of stearic acid. After drying, the mixture was granulated and classified, whereby a preparation having an average particle size of 150 μm was obtained.

The adhesion of the preparations obtained in Examples 3 and 4 were tested in a similar manner to Test 3. As a result, it has been recognized that the adhesion of these preparations depends on pH and has high topical selectivity.

CAPABILITY OF EXPLOITATION IN INDUSTRY

The gastric and/or duodenal mucosa adhesive pharmaceutical composition according to the present invention exhibits pH dependent adhesion so that it adheres directly onto the mucosa of a digestive tract under acid conditions and has high retention in the digestive tract, which makes it possible to release the medicament from the preparation directly to the mucosa of the stomach and/or duodenum; and it also exhibits a controlled release property, which permits continuous release of the medicament and effective transition of the active ingredients into the gastric and/or duodenal mucosa. Sufficient effects can be attained by a smaller dosage so that the preparation has high safety and permits effective use of the active ingredients.

What is claimed is:

1. An adhesive pharmaceutical composition obtained by coating a composition, which comprises a medicament acting at the stomach or duodenum and a water insoluble cellulose polymer (I), with a second composition consisting essentially of a polymer (II) having an adhesive capacity onto the surface of the mucosa of a digestive tract under acid conditions and separates from the mucosa of the digestive tract in neutral or alkaline conditions, wherein said polymer (II) is obtained from an acrylic acid, a methacrylic acid or a mixture thereof, and a carboxylic ester.

2. A pharmaceutical composition according to claim 1, wherein the medicament has been coated with one or more of ingredients selected from the water insoluble polymers, polyglycerin fatty acid esters, lipids and waxes.

3. A pharmaceutical composition according to claim 1, wherein the polymer having adhesive capacity onto the surface of the mucosa of a digestive tract under acid conditions and separating from the mucosa of the digestive tract under neutral or alkaline conditions is soluble in a solution of at least pH 4 and has an anionic group.

4. A pharmaceutical composition according to claim 1, wherein the medicament is selected from the group consisting of antiacids, gastric mucosa protectants, $H_2$ blockers, proton pump inhibitors (PPIs), antibiotics, and urease inhibitors.

5. The pharmaceutical composition as claimed in claim 1, wherein the polymer (II) is a methacrylic acid-methacrylate copolymer.

6. The pharmaceutical composition according to claim 1, wherein said polymer (I) is ethyl cellulose.

7. The pharmaceutical composition according to claim 5, wherein said polymer (I) is ethyl cellulose.

8. The pharmaceutical composition as claimed in claim 1, wherein the polymer (II) is soluble in a solution of at least 4 pH.

9. The pharmaceutical composition according to claim 1, wherein the carboxylic ester is selected from the group consisting of methyl acrylate, ethyl acrylate, n-propyl acrylate, isopropyl acrylate, n-butyl acrylate, isobutyl acrylate, t-butyl acrylate, 2-hydroxyethyl acrylate, 2-hydroxypropyl acrylate, methyl methacrylate, ethyl methacrylate, n-propyl methacrylate, isopropyl methacrylate, 2-hydroxyethyl methacrylate, 2-hydroxypropyl methacrylate, n-butyl methacrylate, isobutyl methacrylate and t-butyl methacrylate.

10. The pharmaceutical composition according to claim 1, wherein the polymer (II) has a methacrylic acid content of from 20 to 60%.

11. The pharmaceutical composition according to claim 1, wherein the second composition further consists essentially of one or more ingredients selected from the group consisting of an excipient, a binder, a plasticizer, a colorant, a corrigent, an adsorbent, an antiseptic, a humectant and an antistatic agent.

12. The pharmaceutical composition according to claim 11, further consisting essentially of an excipient selected from the group consisting of lactose, corn starch, talc, powdered sugar, light anhydrous silicic acid, calcium carbonate and magnesium carbonate.

13. The pharmaceutical composition according to claim 11, further consisting essentially of a binder selected from the group consisting of sucrose, gelatin, powdered acacia, polyvinyl pyrrolidone, pullulan and dextrin.

14. The pharmaceutical composition according to claim 11, further consisting essentially of a plasticizer selected from the group consisting of polyethylene glycol and triethyl citrate.

* * * * *